United States Patent
Liu et al.

(10) Patent No.: US 11,508,101 B2
(45) Date of Patent: Nov. 22, 2022

(54) DYNAMIC DUAL-TRACER PET RECONSTRUCTION METHOD BASED ON HYBRID-LOSS 3D CONVOLUTIONAL NEURAL NETWORKS

(71) Applicant: ZHEJIANG UNIVERSITY, Hangzhou (CN)

(72) Inventors: Huafeng Liu, Hangzhou (CN); Jinmin Xu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 910 days.

(21) Appl. No.: 16/367,012

(22) Filed: Mar. 27, 2019

(65) Prior Publication Data
US 2020/0167974 A1 May 28, 2020

(30) Foreign Application Priority Data
Nov. 28, 2018 (CN) .......................... 201811434410.1

(51) Int. Cl.
G06T 11/00 (2006.01)
A61B 6/03 (2006.01)
G06N 3/04 (2006.01)
G06N 3/08 (2006.01)

(52) U.S. Cl.
CPC ............ *G06T 11/005* (2013.01); *A61B 6/037* (2013.01); *G06N 3/04* (2013.01); *G06N 3/0454* (2013.01); *G06N 3/08* (2013.01); *G06T 2210/41* (2013.01)

(58) Field of Classification Search
CPC .......... A61B 6/037; A61B 6/481; G06N 3/04; G06N 3/0454; G06N 3/0481; G06N 3/08; G06T 11/005; G06T 11/006; G06T 2210/41
See application file for complete search history.

(56) References Cited

FOREIGN PATENT DOCUMENTS

CN 107133997 * 9/2017

OTHER PUBLICATIONS

Separation of a mixture of simultaneous dual-tracer PET signals: a data-driven approach D Ruan, H Liu—IEEE Transactions on Nuclear Science, vol. 64, No. 9, Sep. 2017 (Year: 2017).*

* cited by examiner

Primary Examiner — Amelie R Davis
(74) Attorney, Agent, or Firm — Jiwen Chen; Joywin IP Law PLLC

(57) ABSTRACT

This present invention discloses a dynamic dual-tracer PET reconstruction method based on a hybrid-loss 3D CNN, which selects a corresponding 3D convolution kernel for a 3D format of dual-tracer PET data, and performs feature extraction in a stereoscopic receptive field (down-sampling) and the reconstruction (up-sampling) process, which accurately reconstructs the three-dimensional concentration distributions of two different tracers from the dynamic sinogram. The method of the invention can better reconstruct the simultaneous-injection single-acquisition dual-tracer sinogram without any model constraints. The scanning time required for dual-tracer PET can be minimized based on the method of the present invention.
Using this method, the raw sinogram data of dual tracers can be reconstructed into two volumetric individual images in a short time.

8 Claims, 4 Drawing Sheets

DYNAMIC DUAL-TRACER PET RECONSTRUCTION METHOD BASED ON HYBRID-LOSS 3D CONVOLUTIONAL NEURAL NETWORKS

This application claims the priority benefit of Chinese Application No. 201811434410.1, filed Nov. 28, 2018, which is hereby incorporated by reference.

FIELD OF TECHNOLOGY

The present invention belongs to the field of positron emission tomography (PET) imaging, which involves the 3D convolutional neural networks (CNN) for simultaneous dual-tracer PET imaging.

BACKGROUND

The PET is a kind of functional medical imaging technology used to detect the physiochemical activity in living bodies. The technology is often used to measure the physiological indexes (i.e. glucose metabolism, blood flow, and hypoxia) of the certain parts. The technology of imaging different functions in different parts in the living body mainly relies on various different radioactive tracers. Researchers label the biomacromolecules such as glucose, proteins, nucleic acids required for metabolism in the human body with positron-emitting radioactive isotopes (the most commonly used are $^{11}C$、 $^{13}N$、 $^{15}O$、 $^{18}F$) to make the required radioactive tracers. After the radioactive substance enters the human body by injection or oral administration, the tracers will concentrate in a certain part of the living body according to the physiological or pathological principle. At this time, the radionuclide contained in the tracer itself will decay, producing positron, and the positron will encounter free-moving electrons in the body and the annihilation effect will occur. This annihilation effect produces two high-energy (511 keV) gamma photons propagating in opposite directions. The gamma photons will be detected by a detector outside of the body. The reconstruction algorithm can be used to reconstruct a radioactive concentration distribution image of the tracers in the body.

However, for a specific part of the body, multi-faceted, multi-angle detection can provide more information, and depicting the physiological and functional status of the tumor from different aspects also helps to improve the diagnostic accuracy, so dual-tracer PET imaging is very necessary. In order to save scanning time, reduce patient suffering and improve diagnostic efficiency, single-scan dual-tracer PET dynamic imaging has become a key technology to be solved. Since an annihilation reaction produces a pair of 511 keV gamma photons, the two tracers cannot be distinguished from an energy perspective. The current techniques available for the recovery of dynamic imaging measurements of each individual tracer during dual-tracer PET can be divided into two categories: 1) The first method separates the reconstructed dual-tracer PET image. The method starts from the sinogram data to directly reconstruct the dual-tracer PET image. However, the high computational complexity and dependency on the artificially constructed dual-tracer model make this method less practical clinically applicability. 2) The second method integrates the separation algorithm into the separation process of the dual-tracer PET signals to achieve reconstruction. This method is based on the pre-reconstructed mixed PET image, but the separation accuracy of the method depends largely on the accuracy of the pre-reconstruction and thus limits the further improvement in separation accuracy. In addition, most of the methods are not suitable for the simultaneous injection of two tracers, which is not conducive to maximize scan time, improve machine utilization and reduce patient suffering.

SUMMARY OF THE INVENTION

According to all described above, the present invention provides a dynamic dual-tracer PET reconstruction method based on hybrid-loss 3D CNN. Aim at the 3D volumetric dual-tracer PET sinogram data, the corresponding 3D convolution kernels were adopted to do the convolution operation in the volumetric receptive fields to achieve the dual-tracer reconstruction. The feature extraction (down-sampling) and reconstruction (up-sampling) processes were performed in the stereoscopic field, and the three-dimensional concentration distribution of two different tracers were reconstructed accurately from the dynamic sinogram data.

A dynamic dual-tracer PET reconstruction method based on hybrid-loss 3D CNN, comprising the following steps: (1) injecting mixed dual tracers (tracer I and tracer II) to the subject and performing dynamic PET imaging on the tissue, then obtaining the sequent sinogram data corresponding to different moments to form the three-dimensional dual-tracer concentration distribution, denoted as $S^{dual}$;

(2) injecting sequentially the individual tracer I and tracer II to the same subjects and performing two separate dynamic PET imaging on the tissue respectively, then obtaining two sets of single-tracer sinogram data corresponding to different moments, which are the three-dimensional concentration distribution maps of individual tracer I and tracer II, denoted as $S^I$ and $S^{II}$;

(3) calculating and reconstructing three-dimensional PET image sequences denoted as $X^{Dual}$、 $X^I$ and $X^{II}$ corresponding to the sinogram data $S^{dual}$, $S^I$ and $S^{II}$;

(4) repeating steps (1)-(3) multiple times to generate enough $S^{Dual}$, $X^{Dual}$, $X^I$ and $X^{II}$, and dividing them into training datasets ($S_{train}^{dual}$, $X_{train}^{dual}$, $X_{train}^I$ and $X_{train}^{II}$) and testing datasets ($S_{test}^{dual}$, $X_{test}^I$ and $X_{test}^{II}$);

(5) using $S_{train}^{dual}$ as an input, the corresponding $X_{train}^{dual}$ and $X_{train}^I$ and $X_{train}^{II}$ as the auxiliary label and the main label respectively, then training the three-dimensional convolutional neural networks (3D CNN) to obtain a dynamic dual-tracer PET reconstruction model.

(6) randomly selecting a $S_{test}^{dual}$ from the testing datasets and inputting it into the pre-trained 3D CNN model, and obtaining three-dimensional dynamic PET image sequences $X^I$ and $X^{II}$ corresponding to the tracer I and the tracer II.

Furthermore, the data division in step (4) can be detailed as follows: the sample ratio of the training datasets and testing datasets should be more than 2:1.

Furthermore, the training process through 3D CNN in step (5) can be specified as follows:

5.1 constructing a 3D CNN consisting of a reconstruction network of mixed PET images and a separation network based on pre-reconstructed dual-tracer images;

5.2 initializing the parameters in the described 3D CNN, including the offset vector, weight vector, the learning rate, and the maximum number of iterations of each layer;

5.3 inputting $S^{dual}$ in the training dataset into the 3D CNN one by one for training, and calculating $L_{aux}$ (the difference between the output and the auxiliary label $X^{dual}$) and $L_{main}$ (the difference between the output of the separation network and the main label [$X^I$, $X^{II}$]). Then combining the error $L_{aux}$ and $L_{main}$ to be a total loss function L. Continuously updating the parameters of the entire 3D CNN by adaptive moment estimation (Adam) until the loss function L converges or reaches the maximum number of iterations, thus the training of a dynamic dual-tracer PET reconstruction model can be acquired.

Furthermore, the described reconstructed network consists of two 3D convolution layers, a reshape layer and a concat layer. The output dimension of the reshape layer is the same as the dimension of the input $S^{dual}$, and the output result is used as an input of the concat layer; the concat layer copies and connects the two 3D convolution layers in the third (time) dimension, and the output result is used as an input of the separation network.

Furthermore, the described separation network comprises three down-sampling blocks, three up-sampling blocks and a 3D convolution layer that is sequentially connected in the end.

Furthermore, the down-sampling blocks comprise eight (8) layers. The first layer is a 3D convolution layer and setting the convolution kernel does not change the input dimension size. The second layer is the BatchNorm layer to do the batch-normalization to the output of the first layer. The third layer is the Scale layer to do the zooming and panning of the output of the second layer. The fourth layer is the ReLU layer served as an activity function, and its output is the input of the next 3D convolution layer (the fifth layer). The fifth layer is a 3D CNN layer, and a 2×2×2 convolution kernel is set for down-sampling, and the output is halved with respect to the input dimension. The sixth layer is another BatchNorm layer which normalizes the output of the previous layer. The seventh layer is the Scale layer, which scales and translates the output of the previous layer. The eighth layer is the ReLU layer, which uses the activation function and outputs the result. As the input to the next down-sampling block; after each down-sampling block, the three dimensions of the input are halved.

Furthermore, the up-sampling blocks comprise two layers, the first layer is a 3D deconvolution layer, the convolution kernel is set to double the input dimension, the output result is used as the input of the second layer; the second layer is the 3D convolution layer, and the setting of the convolution kernel does not change the size of the input dimension, and its output is used as the input of the next up-sampling block; after each up-sampling block, the three dimensions of the input are doubled.

Furthermore, the last 3D convolution layer of the separation network has the 1×1×1 kernel. The output of this layer is the output of the entire network, i.e. two individual three-dimensional PET images of tracer I and tracer II.

Furthermore, the total loss function L described can be expressed as:

$$L = L_{aux} + \beta L_{main} = \|X_{train}^{dual} - \widehat{X^{dual}}\|_2^2 + \beta(\|X_{train}^{I} - \widehat{X^{I}}\|_2^2 + \|X_{train}^{II} - \widehat{X^{II}}\|_2^2)$$

wherein the $\| \|_2$ the L2-norm and the $\beta$ is the weight coefficient to adjust the proportion between the auxiliary loss $L_{aux}$ and the main loss $L_{main}$.

The method of the present invention can better reconstruct the dual-tracer sinogram data of simultaneous injection with single acquisition without any model constraints. The scanning time required for dual-tracer PET can be minimized based on the method of the present invention. In addition, a mixed dynamic sinogram can be input into the trained network model, and two single tracers can be output in a short time.

BRIEF DESCRIPTION OF THE DRAWINGS

FIG. 2 (b) is the Zubal thorax phantom of the present invention.

FIG. 3 (b) is the estimated result of the $9^{th}$ frame of [$^{11}$C]DTBZ of the present invention.

FIG. 3 (c) is the ground truth of the $9^{th}$ frame of [$^{11}$C]FMZ of the present invention.

FIG. 3 (d) is the estimated result of the $9^{th}$ frame of [$^{11}$C]FMZ of the present invention.

FIG. 4 (b) is the estimated result of the $9^{th}$ frame of [$^{62}$Cu] ATSM of the present invention.

FIG. 4 (c) is the ground truth of the $9^{th}$ frame of [$^{62}$Cu] PTSM of the present invention.

FIG. 4 (d) is the estimated result of $9^{th}$ frame of [$^{62}$Cu] PTSM of the present invention.

DETAILED DESCRIPTION OF THE EMBODIMENTS OF THE INVENTION

In order to describe the present invention clearly, the detailed instructions are provided in conjunction with the attached figures.

The present invention is based on a dynamic dual-tracer PET reconstruction method of a hybrid-loss 3D CNN, comprising the following steps:

(1) Preparation of the training datasets 1.1 injecting mixed dual tracers (tracer I and tracer II) to a subject and performing dynamic PET imaging on its tissue, then obtaining a sequent sinogram data corresponding to different moments to form a three-dimensional dual-tracer concentration distribution, denoted as $S^{dual}$;

1.2 injecting sequentially the individual tracer I and tracer II to the same subject and performing two separate dynamic PET imaging on the tissue respectively, then obtaining two sets of single-tracer sinogram data corresponding to different moments, which are the three-dimensional concentration distribution maps of individual tracer I and tracer II, denoted as $S^{I}$ and $S^{II}$;

1.3 calculating and reconstructing three-dimensional PET image sequences denoted as $X^{Dual}$、$X^{I}$ and $X^{II}$ corresponding to the dynamic sinogram data $S^{dual}$, $S^{I}$ and $S^{II}$;

1.4 repeating steps (1)~(3) to generate enough sequences of dynamic PET images $S^{Dual}$, $X^{Dual}$, $X^{I}$ and $X^{II}$.

(2) Datasets division into Training Dataset and Testing Datasets extracting two thirds (⅔) of the $S^{Dual}$, $X^{Dual}$, $X^{I}$ and $X^{II}$ data as the training datasets input $S_{train}^{dual}$, the auxiliary label $X_{train}^{dual}$ and the main label $X_{train}^{I}$、$X_{train}^{II}$, respectively The remaining one thirds (⅓) data is the testing datasets $S_{test}^{dual}$ and the corresponding real image value $X_{train}^{I}$ and $X_{train}^{II}$ used for follow-up valuation. The format of main label and real image value are:

[$X_{train}^{I}$, $X_{train}^{II}$]
[$X_{test}^{I}$, $X_{test}^{II}$]

(3) Construction of hybrid-loss 3D CNN

Figure 1:
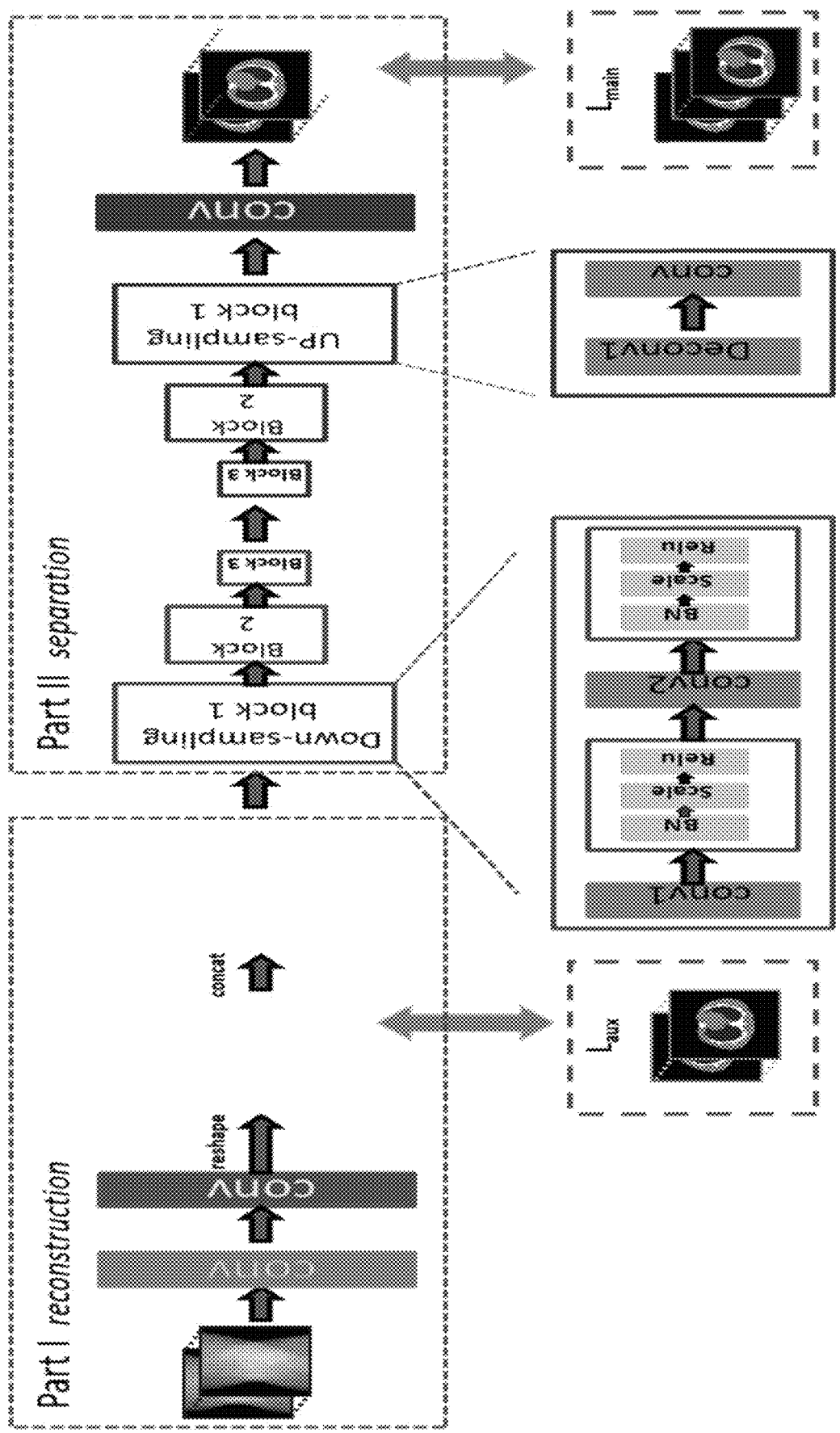
FIG. 1 is the flow diagram of the 3D convolutional neural networks of the present invention.

Constructing a 3D CNN consisting of two parts: the reconstruction of the mixed PET image (Part I) and the separation based on the pre-reconstructed mixed image (Part 4), as shown in FIG. 1.

3.1 reconstructing Part I, which consists of two 3D convolution layers, a reshape layer and a concat layer, using the auxiliary loss function for supervision. The first 3D convolution layer with a 64×1×1 kernel size generates 64 feature maps as input to the next layer. The second 3D convolution layer's kernels have a size of 64×64×1, and generate 4096 feature maps, as the input for the next layer. The reshape layer reassembles the output feature map into a three-dimensional image of the same size as the input $S_{train}^{dual}$, and the output is used as the input of the concat layer; the concat layer copies the output of the two 3D convolution layers in the time dimension as Part II input.

3.2 The separation Part II consists of three down-sampling blocks, three up-sampling blocks and a convolution layer. The composition of a down-sampling block is: the first layer is the 3D convolution layer with 3×3×17 kernels without changing the size of the input dimension, and generates 18 feature maps as input to the next layer. The second layer is the BatchNorm layer to do the batch-normalization to the output of the first layer. The third layer is the Scale layer to do the zooming and panning of the output of the second layer. The fourth layer is the ReLU layer served as an activity function, and its output is the input of the next 3D convolution layer. The fifth layer is a 3D convolution layer, and the down-sampling of the 2×2×2 convolution kernel is set, and the output is halved with respect to the input dimension. The sixth layer is the BatchNorm layer, and the output of the upper layer is normalized. The seventh layer is the Scale layer, the output of the previous layer is scaled and translated. The eighth layer is the ReLU layer, and its output is the input of the next down-sampling block. After each down-sampling block, the three dimensions are halved, the numbers of the three feature maps of the down-sampling block are set to 18, 36 and 72, respectively.

The composition of the up-sampling block is: the first layer is the 3D deconvolution layer with 2×2×2 kernels, through which the size of feature maps will be doubled. The second layer is a 3D convolution layer with 3×3×17 kernels, without changing the input dimensions as the input for the next up-sampling block. Through every up-sampling block, the three dimensions are doubled, and the number of feature maps for the three up-sampling blocks is set to 72, 36 and 18, respectively.

3.3 The last layer is a 3D convolution layer, the kernel size of which is 1×1×1. A feature map is generated as the output of the entire network, in tandem for the two tracer three-dimensional images in the time dimension.

(4) Initialize the network and set training related parameters:

setting the weight matrix and offset vector of each layer to 0, the optimization mode to Adam, the learning rate to $10^{-6}$, the batchsize to 1, and the scaling factor β between $L_{aux}$ and $L_{main}$ to 5.

(5) The training dataset is input into this network for training. The training process is as follows:

inputting the training datasets (input $S_{train}^{dual}$, auxiliary label $X_{train}^{dual}$, main label $X_{train}^{I}$, $X_{train}^{II}$) into the network to do the training procedure, and simultaneously calculating the auxiliary error $L_{aux}$ (the difference between the output error of Part I $\widehat{x^{dual}}$ and the auxiliary label $X_{train}^{dual}$), the main error $L_{main}$ (the difference between the output result of the second part [$\widehat{x^I}$, $\widehat{x^{II}}$] and the main label [$X_{train}^{I}$, $X_{train}^{II}$], The two parts of the loss are combined into the total error function L as follows the loss function is:

$$L = L_{aux} + \beta L_{main} = \|X_{train}^{dual} - \widehat{x^{dual}}\|_2^2 + \beta(\|X_{train}^{I} - \widehat{x^I}\|_2^2 + \|X_{train}^{II} - \widehat{x^{II}}\|_2^2)$$

wherein the first item is the 2-norm of the differences between the reconstructed dual-tracer images $\widehat{x^{dual}}$ and the auxiliary labels $X_{train}^{dual}$, as the auxiliary loss $L_{aux}$. The second item is the sum of the two norms between the predicted value of the tracer I and the tracer II $\widehat{x^I_{train}}$, $\widehat{x^{II}_{train}}$ and its true values $X_{train}^{I}$, $X_{train}^{II}$, as the main error term $L_{main}$, β is a weighting factor used to adjust the proportional relationship between $L_{aux}$ and $L_{main}$.

Next, we demonstrate the reconstruction results of the method of the present invention by simulation experiment.

(1) Phantom selection

Figure 2B:
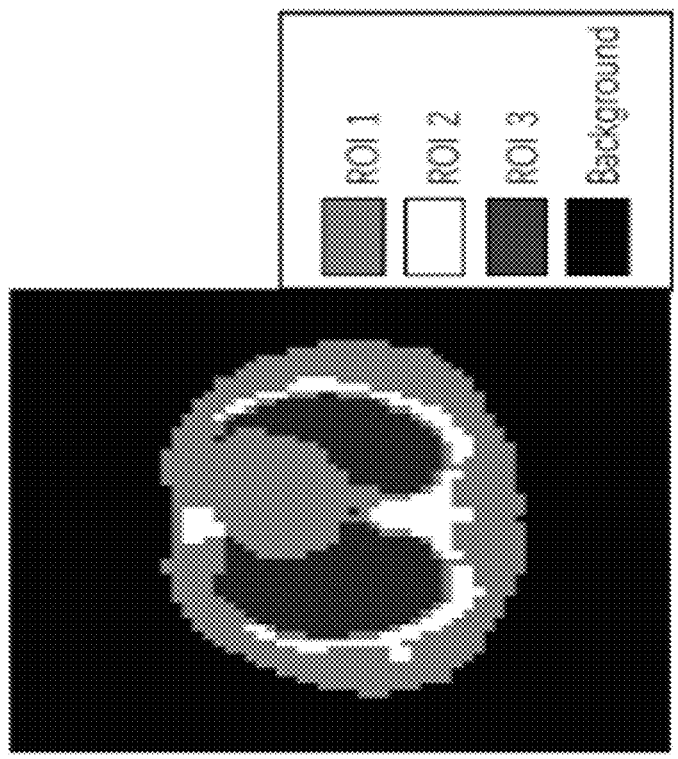
FIG. 2 (a) is the complex brain phantom of the present invention.
Figure 2A:
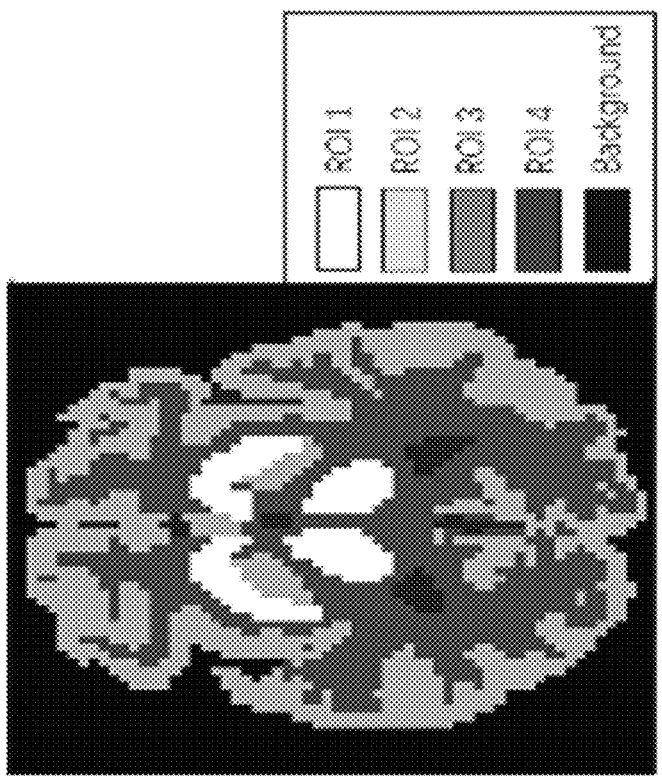

There are two different dual tracers in training datasets, and every group is equipped with different phantoms. Each phantom is composed of three or four Regions of Interest (ROIs) that represent different biochemical environments. In each ROI, the kinetic parameters are different, which indicate different biochemical environment. FIG. 2 (a) is a complex brain phantom containing four regions of interest, the tracer group of [$^{11}$C] FMZ+[$^{11}$C] DTBZ uses this phantom; FIG. 2 (b) is the Zubal thorax phantom and the tracer group of [$^{62}$Cu] ATSM+[$^{62}$Cu] PTSM use this phantom.

(2) The simulation of PET concentration distribution after the tracers entered into the body.

The parallel two-compartment model based on kinetic parameters was used to simulate the movement of the dual-tracer in vivo, and the dynamic differential equations were used to solve the stable concentration profile of the radionuclide after decay. Two two-compartment model based on kinetic parameters were used to simulate the individual tracer in the same way. They simulate the movement of each single tracer in the body, and use the kinetic differential equations to solve the stable concentration profile of tracer I and tracer II after decay in vivo.

(3) The simulation of PET scanning

This experiment uses GATE to do the Monte Carlo simulation and model the PET system. It can simulate the entire acquisition process of PET. The simulation model is SHR74000, which is a whole body PET/CT imaging system designed by Hamamatsu Photonics Co., Ltd., SHR74000—The PET scanner has six crystal rings, each of which includes 48 detector modules, each of which contains a 16×16 array of LYSO crystals with a radius of 826 mm. When three sets of dual tracers and a single tracer concentration profile are entered into the Monte Carlo system, a corresponding dynamic count sequence can be generated.

(4) Reconstruction process: the sinogram is reconstructed using the classical ML-EM reconstruction algorithm to obtain the concentration distribution of the simulated radiotracer pair in the body.

(5) Training process; ⅔ is extracted from the simulation data generated by ([$^{11}$C] FMZ+[$^{11}$C] DTBZ and [$^{62}$Cu] ATSM+[$^{62}$Cu] PTSM) as training data input into the network.

(6) Testing process; use the remaining ⅓ to verify the validity of the network.

Figure 3:
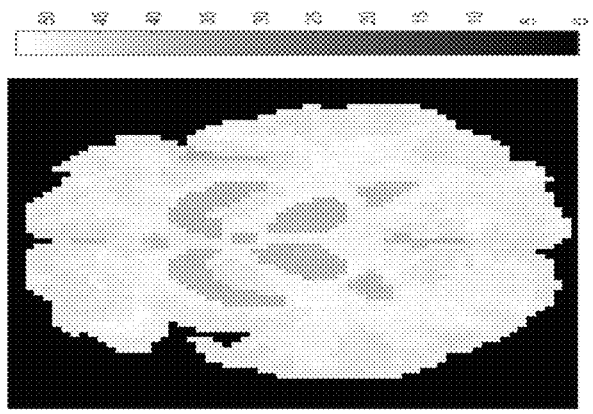
FIG. 3 (a) is the ground truth of the $9^{th}$ frame of [$^{11}$C] DTBZ of the present invention.
Figure 3:
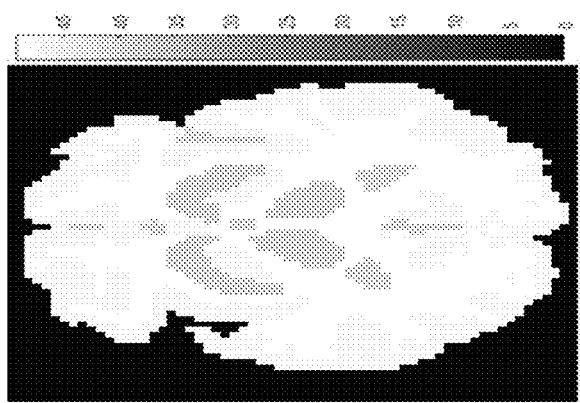
Figure 3:
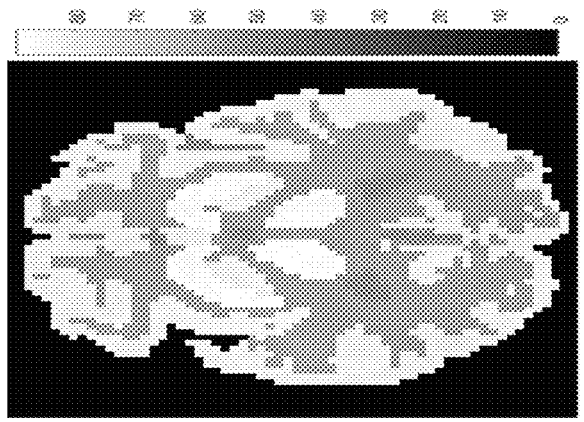
Figure 3:
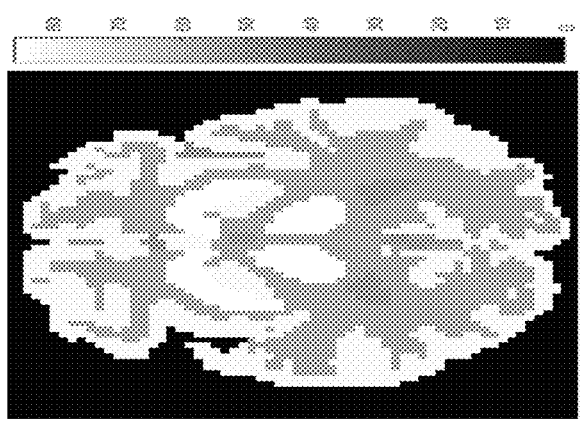

FIG. 3 (a) and FIG. 3 (b) are respectively the simulated radioactive concentration distribution map of the $9^{th}$ frame of [$^{11}$C] DTBZ and the predicted radioactive concentration distribution map obtained by the trained 3D CNN, respectively. FIG. 3 (c) and FIG. 3 (d) are respectively the simulated concentration distribution map of the $9^{th}$ frame of

Figure 4:
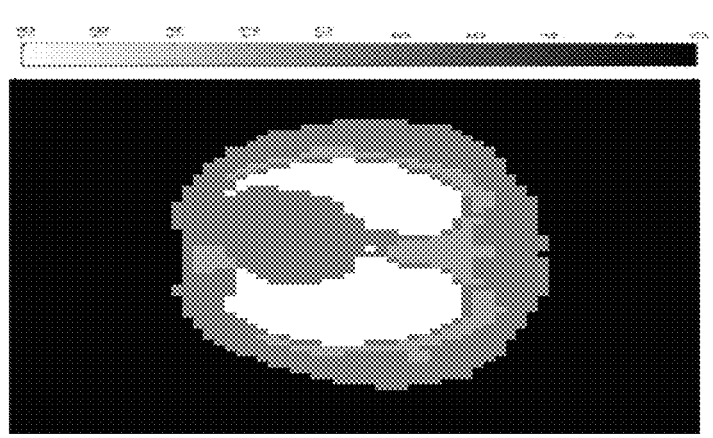
FIG. 4 (a) is the ground truth of the $9^{th}$ frame of [$^{62}$Cu] ATSM of the present invention.
Figure 4:
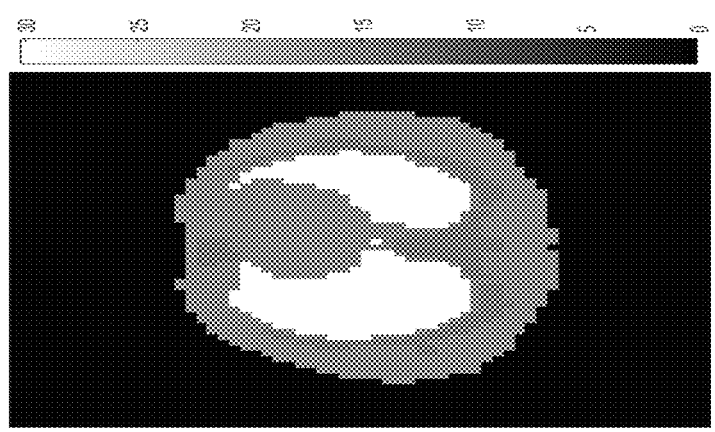
Figure 4:
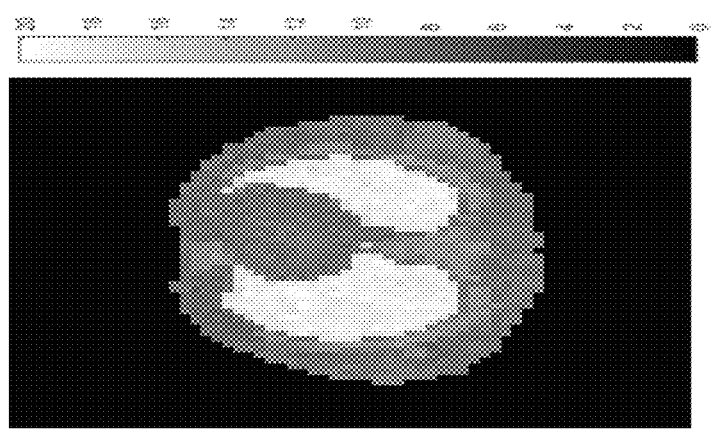
Figure 4:
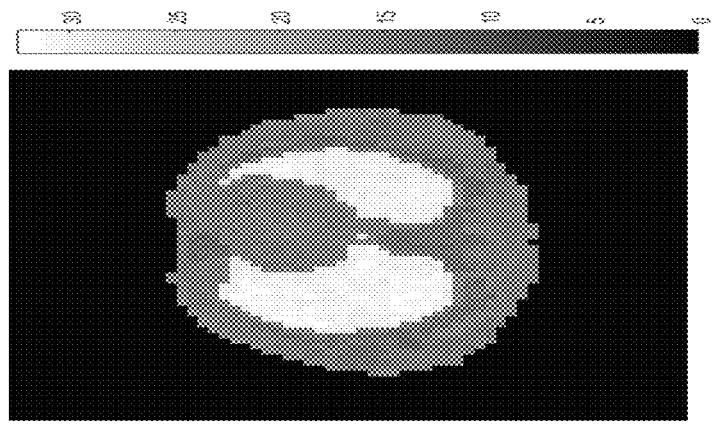

[$^{11}$C] FMZ and the predicted radioactive concentration distribution map obtained by the trained 3D CNN, respectively. FIG. 4 (a) and FIG. 4 (b) are respectively the simulated radioactivity concentration distribution map of the $9^{th}$ frame of [$^{62}$Cu] PTSM and the predicted radioactive concentration distribution map obtained by the trained 3D CNN, respectively. FIG. 5 (c) and FIG. 5 (d) are respectively the simulated concentration distribution map of the $9^{th}$ frame of [$^{62}$Cu] ATSM and the predicted radioactive concentration distribution map obtained by the trained 3D CNN, respectively.

The reconstruction results have shown that the 3D CNN can reconstruct the two individual PET measurements for tracer I and tracer II efficiently.

The description of the specific instances is to facilitate ordinary technicians in the technical field to understand and apply the invention. It is obvious that a person familiar with the technology in this field can easily modify the specific implementation mentioned above and apply the general principles described here into other instances without the creative Labor. Therefore, the invention is not limited to the above instances. According to the disclosure of the invention, the improvement and modification of the invention will be all within the protection scope of the invention.

The invention claimed is:

1. A dynamic dual-tracer position emission tomography (PET) reconstruction method based on hybrid-loss three-dimensional convolutional neural networks (3D CNN), comprising the following steps:
   (1) injecting a mixture of tracer I and tracer II to a subject and performing dynamic PET imaging on its tissue, obtaining a sequent sinogram data corresponding to different moments, and forming a three-dimensional dynamic dual-tracer concentration distribution, denoted as $S^{dual}$;
   (2) sequentially injecting the individual tracer I and tracer II to the subject and performing two separate dynamic PET image acquisitions on the tissue respectively, then obtaining two sets of single-tracer sinogram data, which are three-dimensional concentration distribution maps of individual tracer I and tracer II, respectively denoted as $S^I$ and $S^{II}$;
   (3) calculating and reconstructing three-dimensional PET image sequences denoted as $X^{Dual}$, $X^I$ and $X^{II}$, respectively corresponding to the dynamic sinogram data $S^{dual}$, $S^I$ and $S^{II}$;
   (4) repeating steps (1)-(3) multiple times to generate multiple $S^{Dual}$, $X^{Dual}$, $X^I$ and $X^{II}$, and dividing them into training datasets ($S_{train}^{dual}$, $X_{train}^{dual}$, $X_{train}^I$ and $X_{train}^{II}$) and testing datasets ($S_{test}^{dual}$, $X_{test}^I$ and $X_{test}^{II}$);
   (5) using $S_{test}^{dual}$ as an input, a corresponding $X_{test}^{dual}$ as an auxiliary label and a corresponding $X_{train}^I$ and $X_{train}^{II}$ as a main label, then training the 3D CNN to obtain a dynamic dual-tracer PET reconstruction model; and
   (6) randomly selecting a $S_{test}^{dual}$ from the testing datasets and inputting the $S_{test}^{dual}$ into the selected pre-trained 3D CNN model, and obtaining three-dimensional dynamic PET image sequences $X^I$ and $X^{II}$, respectively corresponding to the tracer I and the tracer II.

2. The method according to claim 1, characterized in that: in the step (4), a sample ratio of the training datasets and the test datasets is greater than two.

3. The method according to claim 1, wherein step (5) comprises the following steps:

5.1 constructing a 3D CNN consisting of a reconstruction network of mixed PET images and a separation network based on pre-reconstructed mixed images;
   5.2 initializing parameters in the 3D CNN, including an offset vector, a weight vector, a learning rate, and a maximum number of iterations of each layer;
   5.3 inputting $S_{test}^{dual}$ in the training dataset into the 3D CNN for training, and calculating the difference between the output of the reconstruction network and the auxiliary label $X^{dual}$ (error $L_{aux}$) and the difference between the output result of the separation network and the main label [$X^I$, $X^{II}$](error $L_{main}$), wherein the error $L_{aux}$ and $L_{main}$ are combined into a total loss function L; and continuously updating the parameters of the entire 3D CNN by adaptive moment estimation (Adam) until the loss function L converges or reaches the maximum number of iterations, thus completing the training to obtain the dynamic dual-tracer PET reconstruction model.

4. The method according to claim 3, characterized in that: the reconstructed network comprises two 3D convolution layers, a reshape layer and a concat layer; wherein the output dimension of the reshape layer is the same as the dimension of the input $S^{dual}$, and the output result of the reshaped layer is used as an input of the concat layer; the concat layer copies and connects the two 3D convolution layers in the time dimension, and the output result of the concat layer is used as an input of the separation network.

5. The method according to claim 3, characterized in that: the separation network comprises three down-sampling blocks, three up-sampling blocks and a 3D convolution layer that are serially connected.

6. The method according to claim 5, characterized in that: each of the down-sampling blocks comprises eight (8) layers: the first layer is a 3D convolution layer; the second layer is a BatchNorm layer to do a batch-normalization to an output of the first layer; the third layer is a Scale layer to do zooming and panning of an output of the second layer; the fourth layer is a ReLU layer serving as an activity function, and its output is an input of the fifth layer; the fifth layer is a 3D CNN layer, and a 2×2×2 convolution kernel is set for down-sampling, and an output of the fifth layer is halved with respect to an input dimension of the fifth layer; the sixth layer is another BatchNorm layer which normalizes the output of the fifth layer; the seventh layer is a Scale layer, which scales and translates the output of the sixth layer and the eighth layer is a ReLU layer, which uses an activation function and outputs a result as an input to a next down-sampling block or when there is no further down-sampling block downstream of the eighth layer, the result of the eighth layer is outputted to an up-sampling block that is downstream of the eighth layer; and wherein, after each down-sampling block, the three dimensions of the input are halved.

7. The method according to claim 5, characterized in that: the up-sampling blocks comprise two layers, the first layer is a 3D deconvolution layer, a convolution kernel is set to double an input dimension of the first layer, an output result of the first layer is used as an input of a second layer; the second layer is a 3D convolution layer, and setting of a convolution kernel in the second layer does not change the size of an input dimension of the second layer, and an output of the second layer is used as an input of the next up-sampling block or when there is no further up-sampling block downstream of the second layer, the result of the second layer is outputted to the 3D convolution layer that is downstream of the second layer; wherein, after each up-sampling block, the three dimensions of the input are doubled.

8. The method according to claim 5, characterized in that: the last 3D convolution layer of the separation network has a 1×1×1 kernel; the output last 3D convolution layer of the separation network has a 1×1×1 kernel; and the output the tracer I and the tracer II.

* * * * *